US006989442B2

(12) United States Patent
Vargeese

(10) Patent No.: US 6,989,442 B2
(45) Date of Patent: Jan. 24, 2006

(54) DEPROTECTION AND PURIFICATION OF OLIGONUCLEOTIDES AND THEIR DERIVATIVES

(75) Inventor: Chandra Vargeese, Thornton, CO (US)

(73) Assignee: Sirna Therapeutics, Inc., Boulder, CO (US)

( * ) Notice: Subject to any disclaimer, the term of this patent is extended or adjusted under 35 U.S.C. 154(b) by 122 days.

(21) Appl. No.: 10/194,875

(22) Filed: Jul. 12, 2002

(65) Prior Publication Data

US 2004/0048251 A1    Mar. 11, 2004

(51) Int. Cl.
*C07H 21/04* (2006.01)
*C12Q 1/68* (2006.01)
(52) U.S. Cl. .................................... 536/25.31; 435/6
(58) Field of Classification Search ............. 536/25.31; 435/6
See application file for complete search history.

(56) References Cited

U.S. PATENT DOCUMENTS

| 4,987,071 | A |   | 1/1991  | Chech et al. |
|-----------|---|---|---------|--------------|
| 5,334,711 | A |   | 8/1994  | Sproat |
| 5,552,539 | A |   | 9/1996  | Duplaa et al. |
| 5,625,047 | A |   | 4/1997  | Been et al. |
| 5,627,053 | A |   | 5/1997  | Usman et al. |
| 5,631,359 | A |   | 5/1997  | Chowrira et al. |
| 5,631,360 | A |   | 5/1997  | Usman et al. |
| 5,672,695 | A |   | 9/1997  | Eckstein et al. |
| 5,686,599 | A | * | 11/1997 | Tracz ............... 536/25.31 |
| 5,716,824 | A |   | 2/1998  | Beigelman et al. |
| 5,804,683 | A |   | 9/1998  | Usman et al. |
| 5,831,071 | A |   | 11/1998 | Usman et al. |
| 5,977,343 | A |   | 11/1999 | Tracz |

FOREIGN PATENT DOCUMENTS

| EP | 0360257  | 3/1990  |
|----|----------|---------|
| WO | 91/03162 | 10/1991 |
| WO | 95/23225 | 8/1995  |
| WO | 93/15187 | 7/1997  |
| WO | 92/07065 | 9/1997  |
| WO | 98/28317 | 7/1998  |
| WO | 98/13526 | 12/1998 |
| WO | 99/16871 | 4/1999  |
| WO | 98/58057 | 9/1999  |
| WO | 98/58058 | 9/1999  |
| WO | 99/55857 | 11/1999 |

OTHER PUBLICATIONS

Wincott et al, Nucleic Acid Research, 1995, 23(14), 2677-2684.*
Cech, 1992, *Nucleic Acids Research*, 17, 7381-7393.
Francklyn and Schimmel, 1989, *Nature*, 337, 478-481.
Cook et al., 1991, *Nucleic Acids Research*, 19, 1577-1583.
Gold, 1988, *Annu. Rev. Biochemistry*, 57, 199-233.
Karaoglu and Thurlow, 1991, *Nucleic Acids Research*, 19, 5293-5300.
Johnson and Benkovic, 1990, *The Enzymes*, vol. 19, Sigman and Boyer, eds., 159-211.
Wincott et al., 1995, *Nucleic Acids Research*, 23, 2677-2684.
Sproat et al., 1995, *Nucleosides and Nucleotides*, 14, 255-273.
Vargeese et al., 1998, *Nucleic Acids Research*, 26, 1046-1050.
Reddy et al., 1995, Tetrahedron Letrt., 36, 8929-8932.
Reddy et al., 1994, Tetrahedron Lett., 35, 4311-4314.
Usman et al., 1987, *J. Am. Chem. Soc.*, 7845-7854.
Scaringe et al., 1990, *Nucleic Acids Research*, 18, 5433-5341.
Hogrefe et al., 1994, Nucleic Acids Research, 21, 4739-4741.
Gasparutto et al., 1992, *Nucleic Acids Research*, 20, 5159-5166.
Westman et al., 1994, Nucleic Acids Research 22, 2430-2431.
Beaudry et al., 2000, *Chemistry and Biology*, 7, in press.
Beigelman et al., 1995, *Nucleic Acids Research*, 23(21), 4434-4442.
Brown et al., 1952, *J. Chem. Soc., London*, 2708.
Egholm et al., 1993 *Nature* 365, 566.
Stein and Cheng, 1993 *Science* 261, 1004.
Kore et al., 1998, *Nucleic Acids Research*, 26(18), 4116-4120.
Torrence et al., 1993 *Proc. Natl. Acad. Sci. USA* 90, 1300.
Duval-Valentin et al., 1992 *Proc. Natl. Acad. Sci USA* 89, 504.
Sullenger et al., 1990, *Cell*, 63, 601-608.
Tsai et al., 1992 *Proc. Natl. Acad. Sci. USA* 89, 8864-8868.
Zaug et al., 324, *Nature* 429 1986.
Kim et al., 84 *Proc. Natl. Acad. Sci. USA* 8788, 1987.
Haseloff and Gerlach, 334 *Nature* 585, 1988.
Cech, 260 *JAMA* 3030, 1988.
Jefferies et al., 17 *Nucleic Acids Research* 1371, 1989.
Usman & McSwiggen, 1995 *Ann. Med. Chem.* 30, 285-294.
Christoffersen and Marr, 1995 *J. Med. Chem.* 38, 2023-2037.
Orgel, 1979, *Proc. R. Soc. London*, B 205, 435.
Joyce, 1989, *Gene*, 82, 83-87.
Beaudry et al., 1992, Science 257, 635-641.
Joyce, 1992, *Scientific American* 267, 90-97.
Breaker et al., 1994, *TIBTECH* 12, 268.
Bartel et al., 1993, *Science* 261: 1411-1418.
Szostak, 1993, TIBS 17, 89-93.
Kumar et al., 1995, *FASEB J.*, 9, 1183.
Breaker, 1996, *Curr. Op. Biotech.*, 7, 442.

(Continued)

*Primary Examiner*—James O. Wilson
*Assistant Examiner*—Ganapathy Krishnana
(74) *Attorney, Agent, or Firm*—McDonnell Boehnen Hulbert & Berghoff LLP

(57) ABSTRACT

Method for synthesis, one-pot deprotection, and purification of molecules comprising one or more ribonucleotides.

24 Claims, 5 Drawing Sheets

OTHER PUBLICATIONS

Santoro et al., 1997, *Proc. Natl. Acad. Sci.*, 94, 4262.
Tang et al., 1997, *RNA* 3, 914.
Nakamaye & Ekstein, 1994, supra.
Long & Uhlenbeck, 1994, supra.
Ishizaka et al., 195, supra.
Vaish et al., 1997, *Biochemistry* 36, 6495.
Uhlenbeck, 1987 *Nature* 328, 596.
Dreyfus, 1988, *Einstein Quart. J. Bio. Med.*, 6, 92.
Warashina et al., 1999, *Chemistry and Biology*, 6, 237-250.
Rossi et al., 1992, *Aids Research and Human Retroviruses* 8, 183.
Usman et al., 1996, *Curr. Op. Struc. Biol.*, 1, 527.
Hampel and Tritz, 1989 *Biochemistry* 28, 4929.
Hampel et al., 1990 *Nucleic Acids Res.* 18, 299.
Perrotta and Been, 1992 Biochemistry 31, 16.
Guerrier-Takada et al., 1983 *Cell* 35, 849.
Forster and Altman, 1990 *Science* 249, 783.
Saville and Collins, 1990 *Cell* 61, 685-696.
Saville and Collins, 1991 *Proc. Natl. Acad. Sci. USA* 88, 8826-8830.
Guo and Collins, 1995 *EMBO J*. 14, 368.
Perrault et al., 1990 *Nature* 344, 565.
Pieken et al., 1991 *Science* 253, 314.
Usman and Cedergren, 1992 *Trends in Biochem. Sci.* 17, 334.
Usman and Cedergren, 1992, *TIBS.* 17, 34.
Usman et al., 1994, *Nucleic Acids Symp.* Ser. 31, 163.
Burgin et al., 1996, *Biochemistry*, 35, 14090.
Beigelman et al., 1995, J. Biol. Chem., 270, 25702.
Karpeisky et al., 1998, *Tetrahedron Lett.*, 39, 1131.
Earnshaw and Gait, 1998, *Biopolymers(Nucleic acid Sciences)*, 48, 39-55.
Verma and Eckstein, 1998, *Annu. Rev. Biochem.*, 67, 99-134.
Burlina et al., 1997, *Bioorg. Med. Chem.*, 5, 1999-2010.
Caruthers et al., 1992, *Methods in Enzymology* 211, 3-19.
Beaucage and Iyer, 1993, *Tetrahedron* 49, 1925.
Limbach et al., 1994, *Nucleic Acids Res.* 22, 2183.
Hunziker and Leumann, 1995, *Nucleic Acid Analogues: Synthesis and Properties*, in *Modern Synthetic Methods*, VCH, 331-417.
Mesmaeker et al., 1994, *Novel Backbone Replacements for Oligonucleotides*, in *Carbohydrate Modifications in Antisense Research*, ACS, 24-39.
Wincott et al., 1997, *Methods Mol. Biol.*, 74, 59.
Hogrefe et al., 1993, *Nucleic Acids Res.*, 231, 4739-4741.

\* cited by examiner

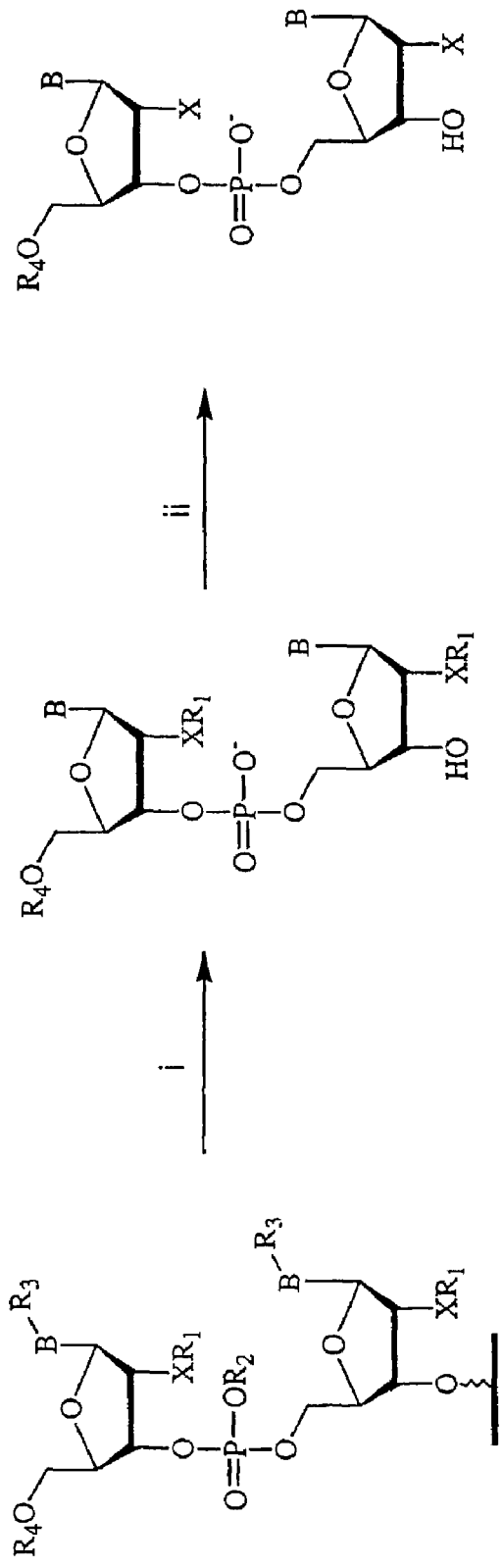
Figure 1: One Pot Deprotection of RNA containing molecules

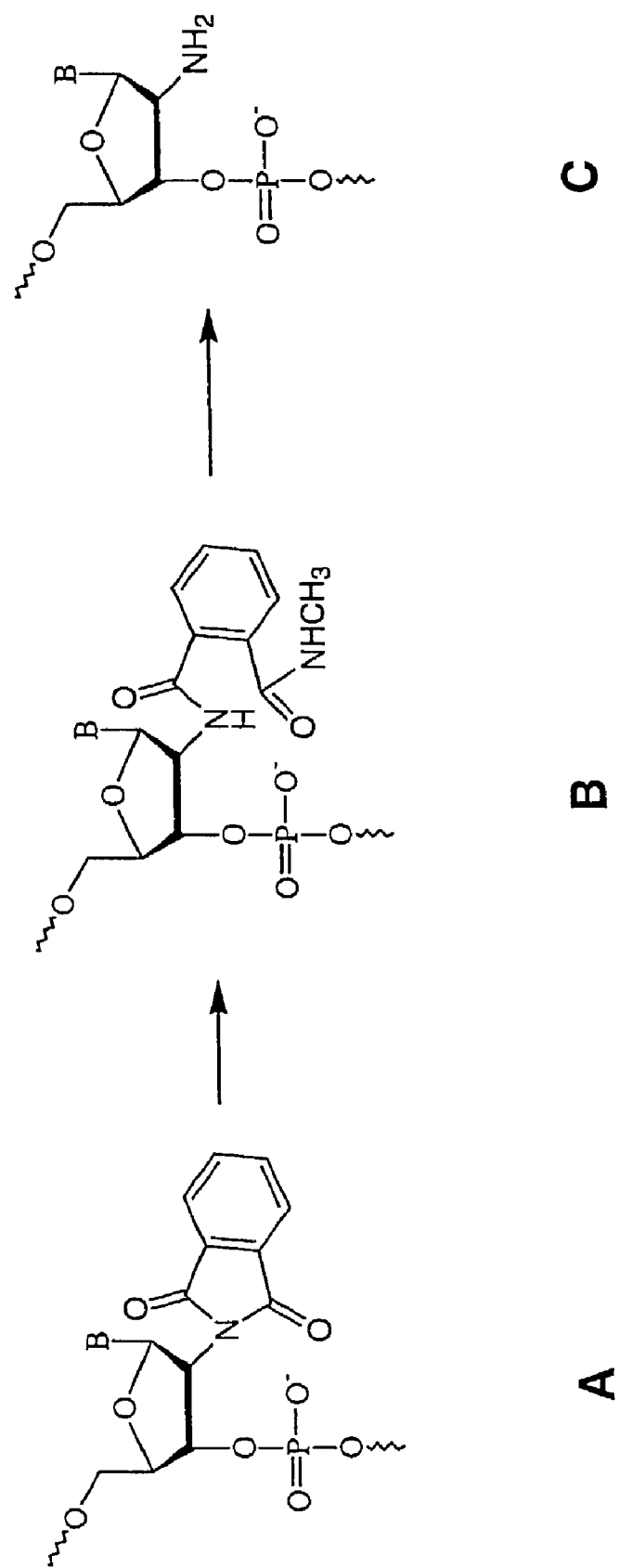
*Figure 2: Incomplete Phthaloyl Deprotection*

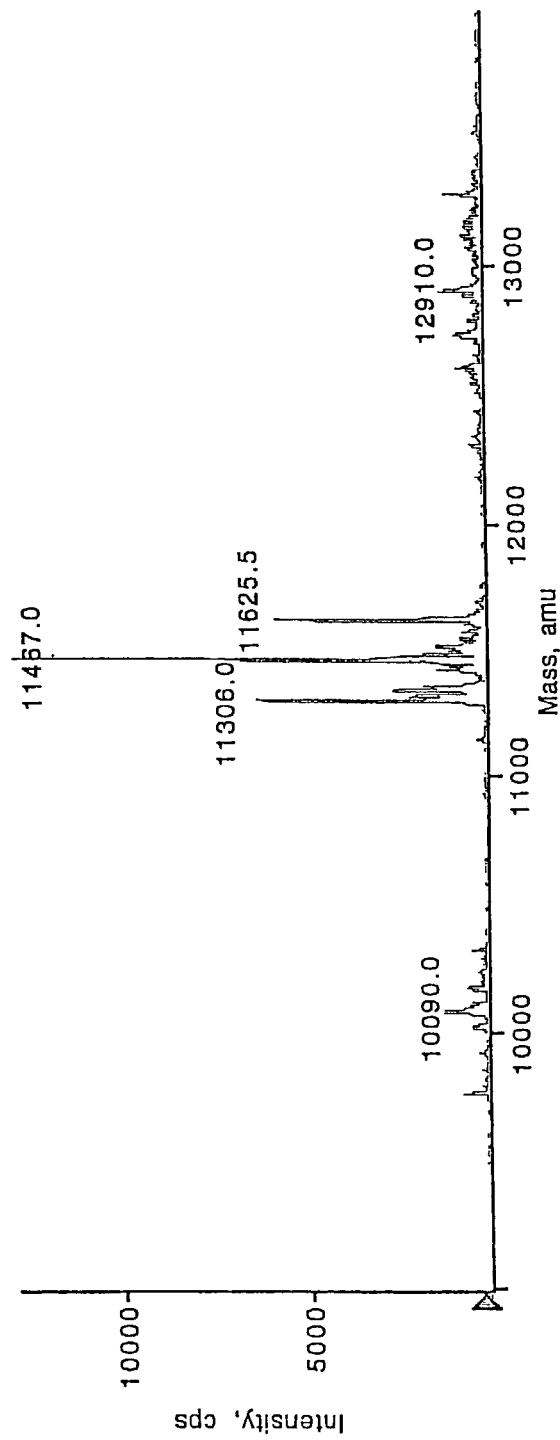
Figure 3A: MS Analysis of RPI.19292 After Anhydrous Deprotection
MA/EtOH/DMSO (15 min. 65 °C)
TEA·3HF (15 min 65 °C)
Trityl-ON purified
MW RPI.19292 = 11,307
MW RPI.19292 = 11,307 + 1 partially cleaved phthaloyl group
MW RPI.19292 = 11307 + 2 partially cleaved phthaloyl groups

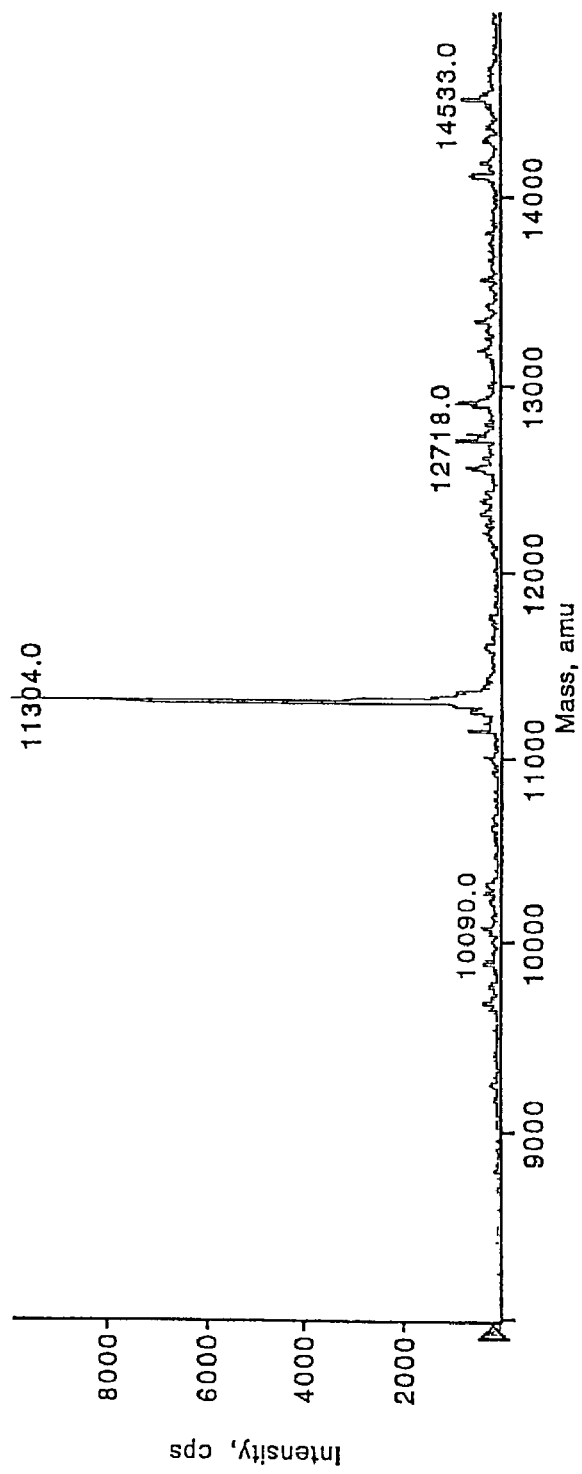
Figure 3B: MS Analysis of RPI.19292 After Aqueous Deprotection
MA/Water/DMSO (15 min. 65 °C)
TEA·3HF (15 min 65 °C)
Trityl-ON purified
MW RPI.19292 = 11,307

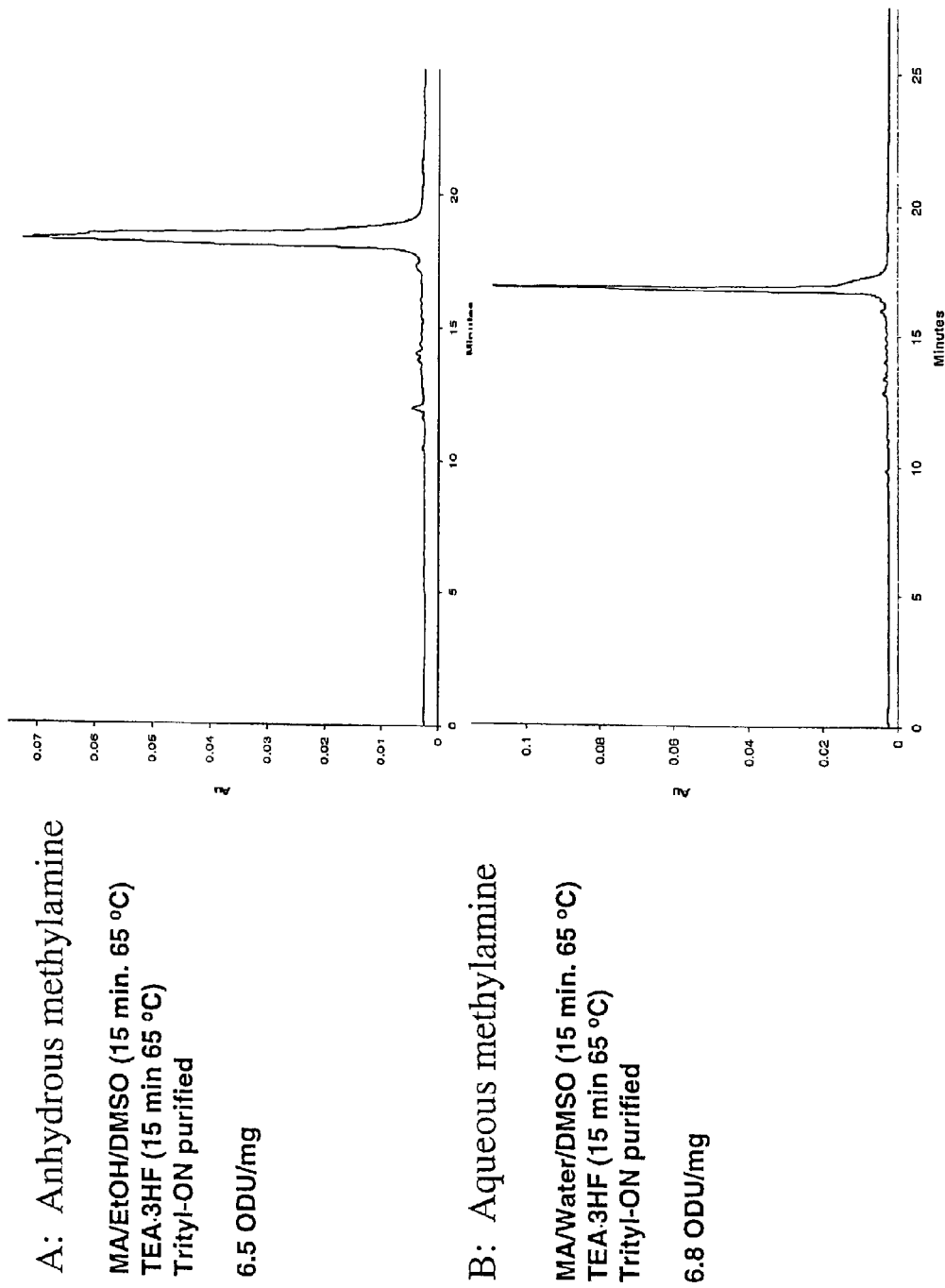

DEPROTECTION AND PURIFICATION OF OLIGONUCLEOTIDES AND THEIR DERIVATIVES

BACKGROUND OF THE INVENTION

This invention relates to the synthesis, deprotection, and purification of molecules comprising one or more ribonucleotides.

The following discussion relates to the synthesis, deprotection, and purification of oligonucleotides containing one or more ribonucleotides. The discussion is not meant to be complete and is provided only for understanding the invention that follows. The summary is not an admission that any of the work described below is prior art to the claimed invention.

Research in the many roles of ribonucleic acids has, in the past, been hindered by limited means of producing such biologically relevant molecules (Cech, 1992, *Nucleic Acids Research*, 17, 7381–7393; Francklyn and Schimmel, 1989, *Nature*, 337, 478–481; Cook et al., 1991, *Nucleic Acids Research*, 19, 1577–1583; Gold, 1988, *Annu. Rev. Biochemistry*, 57, 199–233). Although enzymatic methods existed, protocols that allowed one to probe structure function relationships were limited. Only uniform post-synthetic chemical modification (Karaoglu and Thurlow, 1991, *Nucleic Acids Research*, 19, 5293–5300) or site directed mutagenesis (Johnson and Benkovic, 1990, *The Enzymes*, Vol. 19, Sigman and Boyer, eds., 159–211) were available. In the latter case, researchers were limited to usage of natural bases. Fortunately, adaptation of the phosphoramidite protocol for DNA synthesis to RNA synthesis has greatly accelerated our understanding of RNA. Site-specific introduction of modified nucleotides to any position in a given RNA has now become routine. Furthermore, one is not confined to a single modification but can include many variations in each molecule.

It is seemingly out of proportion that one small structural modification could cause such a dilemma. However, the presence of a single hydroxyl at the 2'-position of the ribofuranose ring, has been the major reason that research in the RNA field has lagged so far behind comparable DNA studies. Progress has been made in improving methods for DNA synthesis that have enabled the production of large amounts of antisense deoxyoligonucleotides for structural and therapeutic applications. Only recently have similar gains been achieved for ribonucleotides (Wincott et al., 1995, *Nucleic Acids Research*, 23, 2677–2684; Sproat et al., 1995, *Nucleosides and Nucleotides*, 14, 255–273; Vargeese et al., 1998, *Nucleic Acids Research*, 26, 1046–1050).

The chasm between DNA and RNA synthesis is due to the difficulty of identifying orthogonal protecting groups for the 5'- and 2'-hydroxyls. Historically, two standard approaches have been taken by scientists attempting to solve the RNA synthesis problem; developing a method that is compatible with state-of the-art DNA synthesis or designing an approach specifically suited for RNA. Although adaptation of the DNA process provides a more universal procedure in which non-RNA phosphoramidites can easily be incorporated into RNA oligomers, the advantage to the latter approach is that one can develop a process that is best for RNA synthesis and as a result, better yields can be realized. However, in both cases similar issues are faced, for example identifying protecting groups that are compatible with synthesis conditions yet can be removed at the appropriate juncture. This problem does not refer only to the 2'- and 5'-OH groups, but includes the base and phosphate protecting groups as well. Consequently, the accompanying deprotection steps, in addition to the choice of ancillary agents, are impacted. Another shared issue is the need for efficient synthesis of the monomer building blocks.

Solid phase synthesis of oligoribonucleotides follows the same pathway as DNA synthesis. A solid support with an attached nucleoside is subjected to removal of the protecting group on the 5'-hydroxyl. The incoming phosphoramidite is coupled to the growing chain in the presence of an activator. Any unreacted 5'-hydroxyl is capped and the phosphite triester is then oxidized to provide the desired phosphotriester linkage. The process is then repeated until an oligomer of the desired length results. The actual reagents used may vary according to the 5'- and 2'-protecting groups. Other ancillary reagents may also differ.

Once the oligoribonucleotide has been synthesized, it must then be deprotected. This is typically a two-step process that entails cleavage of the oligomer from the support and deprotection of the base and phosphate blocking groups, followed by removal of the 2'-protecting groups. Occasionally, a different order of reactions or separate deprotection of the phosphate groups is required. In all cases, it is imperative that indiscriminate removal of protecting groups not occur, this is particularly an issue in the classic situation wherein the first step is base mediated. In this case, if the 2'-hydroxyl is revealed under these conditions, strand scission will result due to attack of the vicinal hydroxyl group on the neighboring phosphate backbone. Two other concerns that are prevalent in RNA synthesis but play no part in DNA are the propensity for 3'-2' phosphodiester migration to provide undesired 2'-5' linkages and the susceptibility of oligoribonucleotides to degradation by ribonucleases. The latter fact has led many researchers to develop 2'-protecting groups that can remain in place until the oligomer is required for the desired experiment.

In the past, deprotection of oligoribonucleotides containing a 2'-O-TBDMS (t-butyldimethylsilyl) group was a two step process that first entailed a basic step similar to that used for the deprotection of DNA in which the oligomer was cleaved from the support and the base and phosphate groups were removed. The initial step was accomplished in 1–4 h at 55° C. with 3/1 $NH_4OH$/EtOH. Since the oligomer is not exposed to severe deprotection conditions for prolonged periods, better yields of higher quality product result. More recently, a faster, two step, deprotection protocol, entailing the use of aqueous methylamine has been reported for RNA (Usman et al., U.S. Pat. No. 5,804,683; Wincott et al., 1995, supra; Reddy et al., 1995, *Tetrahedron Lett.*, 36, 8929–8932). Incubation times have been reduced to 10 min at 65° C. When compared with other RNA deprotection methods, treatment with this reagent gave greater full length product than the standard protocol using 3/1 $NH_4OH$/EtOH (Wincott et al., 1995, supra). The only requirement is that acetyl must be used as the N-protecting group for cytidine because of a well-documented transamination reaction (Reddy et al., 1994, *Tetrahedron Lett.*, 35, 4311–4314). As stated earlier, through the use of methylamine this step has been reduced to 10 minutes. The second step is removal of the 2'-silyl protecting group from the oligonucleotide. In the past this had been accomplished with 1 M n-tetrabutyl ammonium fluoride (TBAF) in THF at room temperature over 24 h (Usman et al., 1987, *J. Am. Chem. Soc.*, 109, 7845–7854; Scaringe et al., 1990, *Nucleic Acids Research*, 18, 5433–5341). Unfortunately, the use of this deprotecting agent produces salts which must be removed prior to analysis and purification. In addition, the long exposure time required for complete removal of the protecting group, coupled with the reagent's sensitivity to adventitious water (Hogrefe et al., 1994, *Nucleic Acids Research*, 21, 4739–4741), made it a less than ideal reagent. Although some reports have been published regarding the use of neat triethylamine trihydrofluoride (TEA.3HF) (Duplaa et al., U.S. Pat. No. 5,552,539, Gasparutto et al., 1992, *Nucleic Acids Research*, 20, 5159–5166; Westman et al., 1994, *Nucleic Acids Research*, 22, 2430–2431) as a desilylating reagent, results have been mixed. A cocktail of TEA.3HF in combination with N-methylpyrrolidinone (NMP) (Usman and Wincott, U.S. Pat. No. 5,831,071; Wincott et al., 1995, supra) or DMF (Sproat et al., 1995, supra) has also been described in which full deprotection can be achieved in 30–90 min at 65° C. or 4–8 h at room temperature. As an added advantage, since no salts are produced, the product can be directly precipitated from the desilylating reagent.

Tracz, U.S. Pat. No. 5,977,343; Tracz, U.S. Pat. No. 5,686,599, describes a one-pot protocol for ribonucleotide deprotection using anhydrous methylamine and triethylamine trihydrogen fluoride. This procedure involves the use of anhydrous methylamine followed by neat triethylamine trihydrofluoride to effectively deprotect oligoribonucleotides in a one-pot fashion. However such a protocol may be cumbersome for deprotection of oligonucleotides synthesized on a plate format, such as a 96-well plate, because it may be necessary to separate the solid-support from the partially deprotected oligonucleotide prior to the 2'-hydroxyl deprotection. Also, since the methylamine solution used is anhydrous, it may be difficult to solubilize the negatively charged oligoribonucleotides obtained after basic treatment. More recently this procedure has been reported in which both the basic deprotection and the desilylation reaction can be accomplished in one-pot using a mixture of anhydrous methylamine in ethanol followed by addition of TEA.3HF (Bellon, 1999, *Current Protocols in Nucleic Acid Chemistry*, Beaucage, Bergstrom, Glick and Jones, eds., in press). This protocol allows for the complete deprotection of an oligoribonucleotide in less than 2 h without any evidence of 3'-2' migration.

The parameters of 2'-deprotection are dictated by the corresponding protecting groups utilized for differing 2'-chemistries present within a given oligonucleotide. The use of alternate 2'-ribofuranosyl carbocycle functions within the same oligonucleotide molecule can present potential problems with respect to the synthesis, deprotection, and purification of such molecules. The efficient synthesis of nucleic acids which are chemically modified to increase nuclease resistance while maintaining catalytic activity is of importance to the potential development of new therapeutic agents. Recently, Beaudry et al., 2000, *Chemistry and Biology*, 7, in press, describe the in vitro selection of a novel nuclease-resistant RNA phosphodiesterase. This enzymatic nucleic acid molecule can contain both ribo (2'-hydroxyl) and amino (2'-deoxy-2'-amino) functions. The large scale synthesis of oligonucleotides with both ribo and amino functions presents practical problems with regard to the concomitant removal of tert-Butyldimethylsilyl (TBDMSi) and N-phthaloyl protecting groups, while at the same time preserving the integrity of the ribonucleotide linkages. The use of the N-phthaloyl protecting group for the 2'-amino group during oligonucleotide synthesis offers the benefit of improved synthetic yields compared to the trifluoroacetyl (TFA) and FMOC groups (Usman et al., U.S. Pat. No. 5,631,360; Beigelman et al., 1995, *Nucleic Acids Research*, 23(21), 4434–4442). The phthaloyl group is readily cleaved with aqueous methylamine at 65° C. and the TBDMSi group is readily cleaved using a fluoride ion source, such as tetrabutylammonium fluoride (TBAF) or triethylammonium trihydrofluoride (TEA.3HF). Application of the "one pot" deprotection procedures described above results in the incomplete deprotection of N-phthaloyl protection. The two step deprotection procedure can be employed for the complete deprotection of oligonucleotides containing both ribo (2'-TBDMS) and amino (N-phthaloyl) protecting groups, however, this process is not readily amenable to large scale oligonucleotide synthesis or multiwell plate oligonucleotide synthesis.

As such there exists an unmet need for a fast, efficient method which allows for the complete deprotection of molecules containing both amino and ribo carbohydrate moieties. Such a method will enable the large scale synthesis of such molecules for use as therapeutic agents and the small scale synthesis of such molecules for combinatorial screening.

SUMMARY OF THE INVENTION

Current oligonucleotide deprotection methods for oligonucleotides comprising one or more ribonucleotides are limited by both the length of time needed for complete deprotection and by the incomplete deprotection of certain protecting groups (for example N-phthaloyl). The use of anhydrous methylamine and triethylamine trihydrofluoride as a "one pot" deprotection cocktail makes use of DMSO to solubilize the partially deprotected oligonucleotide under anhydrous conditions (Tracz, U.S. Pat. No. 5,977,343). The use of aqueous methylamine has been avoided in combination with triethylamine trihydrofluoride up to this point due to the presumed susceptibility of ribonucleotide linkages to degradation under these conditions (for example, see example 3 described herein) as a result of alkaline hydrolysis (Brown et al., 1952, *J. Chem. Soc., London*, 2708). This has been overcome with the separation of the aqueous methylamine treatment from the triethylamine trihydrofluoride treatment by making use of an intermediary drying step to remove the aqueous methylamine reagent prior to removal of the 2'-hydoxyl protecting group, thereby precluding alkaline hydrolysis of the ribonucleotide linkages. This two step process is not amenable to large scale oligonucleotide synthesis and oligonucleotide synthesis performed on a multi-well plate, high throughput format. The use of a "one-pot" deprotection method comprising treatment with anhydrous methylamine and triethylamine trihydrofluoride in the presence of DMSO as a co-solvent is benign to ribonucleotide linkages, however, this process may require additional optimization in terms of both total deprotection time and resulting oligonucleotide quality. In addition, the "one-pot" anhydrous method is not very effective for the complete removal of some protecting groups (for example N-phthaloyl). The deprotection method of the instant invention provides a rapid, "one-pot" method for the complete deprotection of oligonucleotides comprising one or more ribonucleotides, and is further capable of complete deprotection of a wide variety of oligonucleotide protecting groups, including the N-phthaloyl group.

This invention concerns a process for the deprotection and purification of molecules comprising one or more ribonucleotides. Specifically, the present invention features a method for the removal of protecting groups from nucleic acid base, phosphate, and 2'-hydroxyl (2'-OH) and/or 2'-deoxy-2'-amino (2'-$NH_2$) groups, which allows the deprotection and subsequent purification of molecules comprising one or more ribonucleotides in both a large scale and a high throughput manner.

In a preferred embodiment, the invention features a one-pot process for rapid deprotection of molecules comprising one or more ribonucleotides. In additional embodiments, the instant invention features a process for the rapid deprotection of molecules comprising both ribonucleotides and 2'-deoxy-2'-amino ribofuranose moieties which are protected with alkylsilyl and phthaloyl-based protecting groups respectively. Specifically, the invention provides a process for the rapid deprotection of molecules comprising both ribonucleotides and 2'-deoxy-2'-amino ribofuranose moieties which are protected with t-butyldimethylsilyl (TBDMSi) and N-phthaloyl protecting groups respectively In preferred embodiments, the instant invention features the use of an aqueous methylamine solution to partially deprotect molecules comprising one or more ribonucleotides followed by treatment with triethylammonium trihydrofluoride in the presence of a co-solvent (for example, DMSO) for the complete deprotection of molecules.

In a preferred embodiment, the invention features a process for the synthesis, deprotection, and purification of molecules comprising one or more ribonucleotides, comprising the steps of: (a) solid phase, solution phase, and/or hybrid phase, (e.g.; phosphoramidite-based or H-phosphonate-based) oligonucleotide synthesis comprising the steps of detritylation, activation, coupling, capping, and oxidation or the equivalent thereof, in any suitable order, followed by (b) deprotection comprising contacting the nucleic acid molecule having one or more ribonucleotides with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to 100° C., 20° C. to 80° C., 30° C. to 65° C., preferably 35° C. or 65° C. for molecules comprising N-phthaloyl protecting groups, for about 5 to 240 minutes, 20 to 100 minutes, preferably 60 minutes under conditions suitable for partial deprotection of the oligonucleotide, and contacting the partially deprotected molecule comprising one or more ribonucleotides with triethylamine.trihydrofluoride (TEA.3HF) in the presence of a solvent (for example DMSO, DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl), then quenching the deprotection reaction by using aqueous sodium acetate, ammonium bicarbonate, and/or triethylammonium bicarbonate or the equivalent thereof, preferably 50 mM aqueous sodium acetate, then (c) purifying the molecule comprising one or more ribonucleotides, comprising loading the deprotected products onto media comprising Pharmacia Source Q15 and Biorad Macroprep 25Q media, or the equivalent thereof such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes, then lyophilizing the concentrated material.

In an additional preferred embodiment, the invention features a process for the one pot deprotection and subsequent purification of nucleic acid molecules having one or more ribonucleotides with protecting groups, comprising the steps of: (a) deprotection comprising contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to 100° C., 20° C. to 80° C., 30° C. to 65° C., preferably 35° C. or 65° C. for molecules comprising N-phthaloyl protecting groups, for about 5 to 240 minutes, 20 to 100 minutes, preferably 60 minutes under conditions suitable for partial deprotection of the oligonucleotide, and contacting the partially deprotected molecule with triethylamine.trihydrofluoride (TEA.3HF) in the presence of a solvent (for example DMSO, DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl), then quenching the deprotection reaction by using aqueous sodium acetate, ammonium bicarbonate, and/or triethylammonium bicarbonate or the equivalent thereof, preferably 50 mM aqueous sodium acetate, then (b) purifying the molecule comprising one or more ribonucleotides, comprising loading the deprotection products onto media comprising Pharmacia Source Q15 and Biorad Macroprep 25Q media, or the equivalent thereof, such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes, then lyophilizing the concentrated material.

In yet another preferred embodiment, the invention features a process for one pot deprotection of nucleic acid molecules having one or more ribonucleotides with protecting groups, comprising the steps of: (a) contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to 100° C., 20° C. to 80° C., 30° C. to 65° C., preferably 35° C. or 65° C. for molecules comprising N-phthaloyl protecting groups, for about 5 to 240 minutes, 20 to 100 minutes, preferably 60 minutes, under conditions suitable for partial deprotection of the oligonucleotide, and (b) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In a preferred embodiment, the invention features a process for purifying a nucleic acid molecule, comprising the steps of: (a) loading the crude deprotected molecule onto media comprising Pharmacia Source Q15 and Biorad Macroprep 25Q media, or the equivalent thereof such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and (b) applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes.

In an additional preferred embodiment, the nucleic acid molecule is lyophilized after purification.

In preferred embodiments, the deprotection reaction can be quenched by using aqueous sodium acetate, ammonium bicarbonate, and/or triethylammonium bicarbonate or the equivalent thereof, preferably 50 mM aqueous sodium acetate.

In another preferred embodiment, the invention features a process for the deprotection of nucleic acid molecules comprising an oligonucleotide having 2'-N-phthaloyl and 2'-O-silyl protection comprising the steps of: (a) contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to 100° C., 20° C. to 80° C., 30° C. to 65° C., preferably 35° C. or 65° C. for molecules comprising N-phthaloyl protecting groups, for about 5 to 240 minutes, 20 to 100 minutes, preferably 60 minutes, under conditions suitable for partial deprotection of the oligonucleotide, and (b) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In a preferred embodiment, the partially deprotected molecule is filtered using a suitable filtering medium, such as sintered glass, and washed with a polar solvent (for example, DMSO, DMF, ethanol, methanol, isopropanol, and/or N-methylpyrrolidinone) prior to treatment with TEA.3HF reagent. In additional embodiments, the filtrate is cooled prior to treatment with TEA.3HF reagent, preferably to between about 0° C. and −78° C.

In another aspect the invention features a process for oligonucleotide deprotection where the deprotection reaction is performed with the aqueous methylamine solution at temperatures ranging from about 0° C. to 120° C. for a time of about 500 minutes to 5 minutes.

In a preferred embodiment, the process for deprotection of molecules comprising one or more ribonucleotides of the present invention is used to deprotect a molecule synthesized using a column format.

By "column format" is meant, solid phase synthesis wherein the solid support (for example, CPG, polystyrene) is loaded into a retaining device comprising a column, cartridge, or equivalent, which allows the solid support to be sequentially exposed to reagents suitable for the synthesis of polymeric molecules, for example, oligonucleotides and their derivatives.

In an additional preferred embodiment, the process for deprotection of molecules comprising one or more ribonucleotides of the present invention is used to deprotect a molecule synthesized using a multi-well plate format. Specifically, the instant invention provides a high throughput deprotection of oligonucleotides in a multi-well plate format (for example, a 96-well plate or a 256 well plate). More specifically rapid deprotection of enzymatic nucleic acid molecules in greater than microgram quantities with high biological activity is featured. It has been determined that the recovery of enzymatically active nucleic acid molecules in high yield and quantity is dependent upon certain critical steps used during its deprotection.

In additional embodiments, the process for deprotection of molecules comprising one or more ribonucleotides of the present invention is used to deprotect a molecule synthesized in both a trityl-on and trityl-off manner.

By "trityl-on" is meant, a molecule, for example an oligonucleotide, synthesized in a manner which leaves the 5'-terminal dimethoxytrityl protecting group or an equivalent protecting group intact.

By "trityl-off" is meant, a molecule, for example an oligonucleotide, synthesized in a manner which removes the 5'-terminal dimethoxytrityl protecting group or an equivalent protecting group.

By "solid phase" is meant, synthesis comprising a solid support (for example, polystyrene or controlled pore glass) which is used as a scaffold for the sequential addition of subunits in the synthesis of a polymeric molecule such as an oligonucleotide. The solid support can be exposed sequentially to reagents in solution, thereby eliminating the need for repeated purification and isolation steps during synthesis. A linker molecule can be used as an interface between the solid support and the growing polymer. Solid phase synthesis can be used for both phosphoramidite and H-phosphonate methods of oligonucleotide synthesis.

By "solution phase" is meant, synthesis comprising the combining of reactants and reagents in solution, such as in a solvent which provides a homogenious mixture. Solution phase synthesis can be a preferred method for the synthesis of molecules in large quantities in consideration of lower costs, more efficient reactivity of reagents, and engineering factors.

By "hybrid phase" is meant, synthesis comprising both solid phase and solution phase synthesis elements.

The instant invention also features a large scale deprotection method of molecules comprising one or more ribonucleotides (for example, 3 mmol synthesis scale or greater). More specifically rapid deprotection of molecules comprising one or more ribonucleotides in greater than multigram or kilogram quantities with high biological activity is featured. It will be recognized by those skilled in the art that modifications concerning time and temperature parameters can be used to optimize deprotection conditions for reactions of differing scale and/or molecules of differing composition. The use of different time and temperature parameters for varying molecular content and/or different reaction scale applications is hence within the scope of the invention.

In a preferred embodiment, the invention features a method for the purification of nucleic acid molecules of the instant invention. Specifically, the invention features the use of ethanol or acetonitrile, with ethanol preferred, as an organic modifier in the purification of oligonucleotides with anion exchange chromatography. In an additional aspect, the instant invention features the use of ethanol as an organic modifier used in the purification of oligonucleotide molecules, including but not limited to enzymatic nucleic acids.

In additional embodiments, the media used for the purification of nucleic acid molecules of the instant invention comprises Pharmacia Source Q15 and Biorad Macroprep 25Q type media, or the equivalent thereof such as Pharmacia Q-sepharose, Perceptive POROS HQ, TOSOHAAS Q-5PW-HR, Q-5PW, or super Q-5PW. In yet another preferred embodiment, the purification media is equilibrated with a buffer comprising either 20% ethanol or acetonitrile in about 20 mM sodium phosphate and about 0.1 M NaCl.

In additional embodiments, the invention features a loading buffer for oligonucleotide purification comprising either 20% ethanol or acetonitrile in about 20 mM sodium phosphate and about 0.1 M NaCl. In one aspect, the invention concerns applying a suitable gradient of about 1.0 M NaCl as an elution buffer for the purification of nucleic acid molecules of the instant invention. In another embodiment, the invention features the analysis of the fractions resulting from the purification process described herein, by a suitable technique (for example, UV, HPLC, and/or CGE), and allowing for the pure fractions to be pooled and desalted via tangential flow filtration or the equivalent thereof, by using membranes comprising such membranes as those selected from the group consisting of Sartorius or Pall Filtron PES 1 K membranes, In yet another preferred embodiment, the invention features the use of lyophilization as a means to concentrate the purified material.

By RNA is meant a molecule comprising at least one ribonucleotide residue. By "ribonucleotide" is meant a nucleotide with a hydroxyl group at the 2' position of a β-D-ribo-furanose moiety. The RNA can be single, double or multiple stranded and may comprise modified or unmodified nucleotides or non-nucleotides or various mixtures and combinations thereof. The RNA may be an enzymatic nucleic acid, antisense nucleic acid, decoy RNA, aptamer RNA, triplex forming oligonucleotide, chimeric RNA, 2–5A antisense chimera, agonist RNA, antagonist RNA, or any other RNA species. RNA can be used for purposes including but not limited to use as therapeutic agents, diagnostic reagents, and research reagents.

By "nucleic acid", "nucleic acid molecule" or "oligonucleotide" as used herein is meant a molecule having two or more nucleotides. The nucleic acid can be single, double, or multiple stranded and may comprise modified or unmodified nucleotides or non-nucleotides or various mixtures and combinations thereof.

In another preferred embodiment, the invention features a process for the synthesis, deprotection, and purification of an enzymatic nucleic acid molecule, preferably in the hammerhead, AH ribozyme, NCH (Inozyme), G-cleaver, amberzyme, and/or zinzyme motif.

By "enzymatic nucleic acid molecule" it is meant a nucleic acid molecule that has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not meant to be limiting and those skilled in the art will recognize that all that is important in an enzymatic nucleic acid molecule of this invention is that it have a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, JAMA).

By "antisense nucleic acid" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004). Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "AH ribozyme" motif is meant, an enzymatic nucleic acid molecule comprising a motif as described in Kore et al., 1998, *Nucleic Acids Research*, 26(18), 4116–4120.

By "NCH" or "Inozyme" motif is meant, an enzymatic nucleic acid molecule comprising a motif as described in Ludwig et al., U.S. Ser. No. 09/406,643, filed Sep. 27, 1999, entitled "COMPOSITIONS HAVING RNA CLEAVING ACTIVITY", and International PCT publication Nos. WO 98/58058 and WO 98/58057, all incorporated by reference herein in their entirety including the drawings.

By "G-cleaver" motif is meant, an enzymatic nucleic acid molecule comprising a motif as described in Eckstein et al., International PCT publication No. WO 99/16871, incorporated by reference herein in its entirety including the drawings.

By "zinzyme" motif is meant, a class II enzymatic nucleic acid molecule comprising a motif as described in Beigelman et al., International PCT publication No. WO 99/55857, incorporated by reference herein in its entirety including the drawings. Zinzymes represent a non-limiting example of an enzymatic nucleic acid molecule that does not require a ribonucleotide (2'-OH) group within its own nucleic acid sequence for activity.

By "amberzyme" motif is meant, a class I enzymatic nucleic acid molecule comprising a motif as described in Beigelman et al., International PCT publication No. WO 99/55857, incorporated by reference herein in its entirety including the drawings. Amberzymes represent a non-limiting example of an enzymatic nucleic acid molecule that does not require a ribonucleotide (2'-OH) group within its own nucleic acid sequence for activity.

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300).

By "triplex forming oligonucleotide" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, *Cell*, 63, 601–608). This is meant to be a specific example. Those in the art will recognize that this is but one example, and other embodiments can be readily generated using techniques generally known in the art.

By "agonist RNA" is meant an RNA molecule that can bind to protein receptors with high affinity and cause the stimulation of specific cellular pathways.

By "antagonist RNA" is meant an RNA molecule that can bind to cellular proteins and prevent it from performing its normal biological function (for example, see Tsai et al., 1992 *Proc. Natl. Acad. Sci. USA* 89, 8864–8868).

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a is a schematic representation of a one pot deprotection of Molecules comprising one or more ribonucleotides synthesized using the phosphoramidite approach.

FIG. 2 is schematic representation of incomplete N-phthaloyl deprotection products. Compound A represents intact N-phthaloyl protection, compound B represents partially cleaved N-phthaloyl protection, and compound C represents a free 2'-amino group after complete cleavage of N-phthaloyl protection.

FIG. 3 shows a comparison of different one pot deprotection methods based on electrospray mass spectrometry (ESMS) data. FIG. 3A shows a ESMS chromatogram of a purified full length oligonucleotide containing ribonucleotide functions (TBDMS protection) and two 2'-amino functions (N-phthaloyl protection) following a deprotection method which utilized anhydrous methylamine/DMSO/TEA.3HF. FIG. 3B shows a ESMS chromatogram of a purified full length oligonucleotide containing ribonucleotide functions (TBDMS protection) and two 2'-amino functions (N-phthaloyl protection) following a deprotection method which utilized aqueous methylamine/DMSO/TEA.3HF. The three peaks seen in FIG. 3A represents the masses of the fully deprotected oligo, the deprotected oligo with one partially deprotected phthaloyl group intact, and the deprotected oligo with two partially deprotected phthaloyl groups intact. The single peak shown in FIG. 3B represents the mass of the fully deprotected oligo only.

FIG. 4 shows a comparison of different one pot deprotection methods based on capillary gel electrophoresis data. FIG. 4A shows a CE chromatogram of the purified full length oligonucleotide shown in FIG. 3A, which results in a broad peak due to partially cleaved phthaloyl group contaminants. FIG. 4B shows a CE chromatogram of the purified full length oligonucleotide shown in FIG. 3B, which results in a single narrow peak consistent with a homogenous oligonucleotide species.

ENZYMATIC NUCLEIC ACID MOLECULES

The enzymatic RNA molecule is a nucleic acid molecule comprising one or more ribonucleotides. Enzymatic RNA molecule is able to intramolecularly or intermolecularly cleave RNA or DNA and thereby inactivate a target RNA or DNA molecule. The enzymatic RNA acid molecule that has complementarity in a substrate binding region to a specified gene target, also has an enzymatic activity that specifically cleaves RNA or DNA in that target. This complementarity functions to allow sufficient hybridization of the enzymatic RNA molecule to the target RNA or DNA to allow the cleavage to occur. 100% Complementarity is preferred, but complementarity as low as 50–75% may also be useful in this invention. The nucleic acids may be modified at the base, sugar, and/or phosphate groups.

The term enzymatic RNA acid is used interchangeably with phrases such as ribozymes, enzymatic nucleic acid, catalytic RNA, enzymatic RNA, nucleozyme, RNA enzyme, endoribonuclease, minizyme, leadzyme, oligozyme and the like.

By "complementarity" is meant a nucleic acid that can form hydrogen bond(s) with other RNA sequence by either traditional Watson-Crick or other non-traditional types (for example, Hoogsteen type) of base-paired interactions.

RNA molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, *Nature* 429 1986; Kim et al., 84 *Proc. Natl. Acad. Sci. USA* 8788, 1987; Haseloff and Gerlach, 334

Nature 585, 1988; Cech, 260 JAMA 3030, 1988; and Jefferies et al., 17 Nucleic Acids Research 1371, 1989).

Because of their sequence-specificity, trans-cleaving ribozymes show promise as therapeutic agents for human disease (Usman & McSwiggen, 1995 Ann. Rep. Med. Chem. 30, 285–294; Christoffersen and Marr, 1995 J. Med. Chem. 38, 2023–2037). Ribozymes can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic RNA act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. In addition, several in vitro selection (evolution) strategies (Orgel, 1979, Proc. R. Soc. London, B 205, 435) have been used to evolve new nucleic acid catalysts capable of catalyzing cleavage and ligation of phosphodiester linkages (Joyce, 1989, Gene, 82, 83–87; Beaudry et al., 1992, Science 257, 635–641; Joyce, 1992, Scientific American 267, 90–97; Breaker et al., 1994, TIBTECH 12, 268; Bartel et al., 1993, Science 261:1411–1418; Szostak, 1993, TIBS 17, 89–93; Kumar et al., 1995, FASEB J, 9, 1183; Breaker, 1996, Curr. Op. Biotech., 7, 442; Santoro et al., 1997, Proc. Natl. Acad. Sci., 94, 4262; Tang et al., 1997, RNA 3, 914; Nakamaye & Eckstein, 1994, supra; Long & Uhlenbeck, 1994, supra; Ishizaka et al., 1995, supra; Vaish et al., 1997, Biochemistry 36, 6495; all of these are incorporated by reference herein). Each can catalyze a series of reactions including the hydrolysis of phosphodiester bonds in trans (and thus can cleave other RNA molecules) under physiological conditions.

The enzymatic nature of a ribozyme has significant advantages, such as the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of a ribozyme.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al., 324, Nature 429 1986 Uhlenbeck, 1987 Nature 328, 596; Kim et al., 84 Proc. Natl. Acad. Sci. USA 8788, 1987; Dreyfus, 1988, Einstein Quart. J. Bio. Med., 6, 92; Haseloff and Gerlach, 334 Nature 585, 1988; Cech, 260 JAMA 3030, 1988; and Jefferies et al., 17 Nucleic Acids Research 1371, 1989; Santoro et al., 1997 supra).

Because of their sequence specificity, trans-cleaving ribozymes show promise as therapeutic agents for human disease (Usman & McSwiggen, 1995 Ann. Rep. Med. Chem. 30, 285–294; Christoffersen and Marr, 1995 J. Med. Chem. 38, 2023–2037). Ribozymes can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, Chemistry and Biology, 6, 237–250).

In one aspect, enzymatic nucleic acid molecules are formed in a hammerhead or hairpin motif (Table I), but may also be formed in the motif of a hepatitis delta virus (HDV), group I intron, RNaseP RNA (in association with an external guide sequence) or Neurospora VS RNA (Table I). Examples of such hammerhead motifs are described by Rossi et al., 1992, Aids Research and Human Retroviruses 8, 183; Usman et al., 1996, Curr. Op. Struct. Biol., 1, 527; of hairpin motifs by Hampel et al., EP 0360257; Hampel and Tritz, 1989 Biochemistry 28, 4929; and Hampel et al., 1990 Nucleic Acids Res. 18, 299; Chowrira et al., U.S. Pat. No. 5,631,359; an example of the hepatitis delta virus motif is described by Perrotta and Been, 1992 Biochemistry 31, 16; Been et al., U.S. Pat. No. 5,625,047; of the RNaseP motif by Guerrier-Takada et al., 1983 Cell 35, 849; Forster and Altman, 1990 Science 249, 783; Neurospora VS RNA ribozyme motif is described by Collins (Saville and Collins, 1990 Cell 61, 685–696; Saville and Collins, 1991 Proc. Natl. Acad. Sci. USA 88, 8826–8830; Guo and Collins, 1995 EMBO J. 14, 368) and of the Group I intron by Zaug et al., 1986, Nature, 324, 429; Cech et al., U.S. Pat. No. 4,987,071. These specific motifs are not limiting in the invention and those skilled in the art will recognize that all that is important in an enzymatic nucleic acid molecule with endonuclease activity of this invention is that it has a specific substrate binding site which is complementary to one or more of the target gene RNA and that it have nucleotide sequences within or surrounding that substrate binding site which impart an RNA cleaving activity to the molecule. The length of the binding site varies for different ribozyme motifs, and a person skilled in the art will recognize that to achieve an optimal ribozyme activity the length of the binding arm should be of sufficient length to form a stable interaction with the target nucleic acid sequence.

Catalytic activity of the ribozymes described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 Nature 344, 565; Pieken et al., 1991 Science 253, 314; Usman and Cedergren, 1992 Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein).

Chemically synthesizing nucleic acid molecules with modifications (base, sugar and/or phosphate) that prevent their degradation by serum ribonucleases may increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules described herein. All these references are incorporated by reference herein. Modifications which enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al., 1996, *Biochemistry*, 35, 14090). Sugar modifications of nucleic acid molecules have been extensively described in the art (see Eckstein et al., International Publication PCT No. WO 92/07065; Perrault et al. *Nature*, 1990, 344, 565–568; Pieken et al. *Science*, 1991, 253, 314–317; Usman and Cedergren, *Trends in Biochem. Sci.*, 1992, 17, 334–339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic acid Sciences)*, 48, 39–55; Verma and Eckstein, 1998, *Annu. Rev. Biochem.*, 67, 99–134; and Burlina et al., 1997, *Bioorg. Med. Chem.*, 5, 1999–2010; all of the references are hereby incorporated by reference herein in their totalities). Such publications describe general methods and strategies to determine the location of incorporation of sugar, base and/or phosphate modifications and the like into ribozymes without inhibiting catalysis. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications may cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications which maintain or enhance activity are provided. Such nucleic acid is also generally more resistant to nucleases than unmodified nucleic acid. Thus, in a cell and/or in vivo the activity may not be significantly lowered. Therapeutic nucleic acid molecules delivered exogenously must optimally be stable within cells until translation of the target RNA has been inhibited long enough to reduce the levels of the undesirable protein. This period of time varies between hours to days depending upon the disease state. Clearly, nucleic acid molecules must be resistant to nucleases in order to function as effective intracellular therapeutic agents. Improvements in the chemical synthesis of RNA and DNA (Wincott et al., 1995 *Nucleic Acids Res.* 23, 2677; Caruthers et al., 1992, *Methods in Enzymology* 211,3–19 (incorporated by reference herein) have expanded the ability to modify nucleic acid molecules by introducing nucleotide modifications to enhance their nuclease stability as described above.

Use of these the nucleic acid-based molecules of the invention will lead to better treatment of disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of patients with nucleic acid molecules may also include combinations of different types of nucleic acid molecules.

Therapeutic nucleic acid molecules (e.g., enzymatic nucleic acid molecules and antisense nucleic acid molecules) delivered exogenously must optimally be stable within cells until translation of the target RNA has been inhibited long enough to reduce the levels of the undesirable protein. This period of time varies between hours to days depending upon the disease state. Clearly, these nucleic acid molecules must be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

By "enhanced enzymatic activity" is meant to include activity measured in cells and/or in vivo where the activity is a reflection of both catalytic activity and ribozyme stability. In this invention, the product of these properties is increased or not significantly (less than 10-fold) decreased in vivo compared to an all RNA ribozyme or all DNA enzyme.

In yet another preferred embodiment, nucleic acid catalysts having chemical modifications which maintain or enhance enzymatic activity are provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, *Biochemistry*, 35, 14090). Such ribozymes herein are said to "maintain" the enzymatic activity of an all RNA ribozyme.

In another aspect the nucleic acid molecules comprise a 5' and/or a 3'-cap structure.

By "cap structure" is meant chemical modifications, which have been incorporated at either terminus of the oligonucleotide (see, for example, Wincott et al., WO 97/26270, incorporated by reference herein). These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both termini. In non-limiting examples the 5'-cap is selected from the group comprising inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

In yet another preferred embodiment, the 3'-cap is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details, see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

An "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups which are unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups which have an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups may also include aryl, alkylaryl, carbocyclic aryl, heterocyclic aryl, amide and ester groups. An "aryl" group refers to an aromatic group which has at least one ring having a conjugated π electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistry*, 35, 14090; Uhlman & Peyman, supra). By "modified bases" in this aspect is meant nucleotide bases other than adenine, guanine, cytosine and uracil at 1' position or their equivalents; such bases may be used at any position, for example, within the catalytic core of an enzymatic nucleic acid molecule and/or in the substrate-binding regions of the nucleic acid molecule.

In a preferred embodiment, the invention features modified ribozymes with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties,* in *Modern Synthetic Methods,* VCH, 331–417, and Mesmaeker et al., 1994, *Novel Backbone Replacements for Oligonucleotides,* in *Car-* bohydrate Modifications in Antisense Research, ACS, 24–39. These references are hereby incorporated by reference herein.

By "abasic" is meant sugar moieties lacking a base or having other chemical groups in place of a base at the 1' position, (for more details, see Wincott et al., International PCT publication No. WO 97/26270).

By "unmodified nucleoside" is meant one of the bases adenine, cytosine, guanine, thymine, uracil joined to the 1' carbon of β-D-ribo-furanose.

By "modified nucleoside" is meant any nucleotide base which contains a modification in the chemical structure of an unmodified nucleotide base, sugar and/or phosphate.

In connection with 2'-modified nucleotides as described for the present invention, by "amino" is meant 2'-$NH_2$ or 2'-O—$NH_2$, which may be modified or unmodified. Such modified groups are described, for example, in Eckstein et al., U.S. Pat. No. 5,672,695 and Matulic-Adamic et al., WO 98/28317, respectively, which are both incorporated by reference herein in their entireties.

Various modifications to nucleic acid (e.g., antisense and ribozyme) structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Use of these molecules will lead to better treatment of the disease progression by affording the possibility of combination therapies (e.g., multiple ribozymes targeted to different genes, ribozymes coupled with known small molecule inhibitors, or intermittent treatment with combinations of ribozymes (including different ribozyme motifs) and/or other chemical or biological molecules). The treatment of patients with nucleic acid molecules may also include combinations of different types of nucleic acid molecules. Therapies may be devised which include a mixture of ribozymes (including different ribozyme motifs), antisense and/or 2–5A chimera molecules to one or more targets to alleviate symptoms of a disease.

Synthesis and Purification of Oligonucleotides Comprising One or More Ribonucleotide Oligonucleotides comprising one or more ribonucleotides can be chemically synthesized. The method of synthesis used for oligonucleotides comprising one or more ribonucleotides, including certain enzymatic nucleic acid molecules, follows the procedure as described in Usman et al., 1987, *J. Am. Chem. Soc.*, 109, 7845; Scaringe et al., 1990, *Nucleic Acids Res.*, 18, 5433; Wincott et al., 1995, *Nucleic Acids Res.* 23, 2677–2684 and Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 mmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5–99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the oligonucleotide comprising one or more ribonucleotides is performed according to the present invention. Oligonucleotides are purified accoriding to the present invention, and/or by gel electrophoresis using general methods or are purified by high pressure liquid chromatography (HPLC; See Stinchcomb et al., International PCT Publication No. WO 95/23225, the totality of which is hereby incorporated herein by reference) and are resuspended in water. For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the oligonucleotide is detritylated with 0.5% TFA for 13 min. The cartridge is then washed again with water, salt exchanged with 1 M NaCl and washed with water again. The oligonucleotide is then eluted with 30% acetonitrile.

Deprotection of Oligonucleotides Comprising One or More Ribonucleotides

For large scale and high throughput chemical synthesis of oligoribonucleotides, it is important that the two main steps involved in the deprotection of oligoribonucleotides (i.e. basic treatment to remove amino protecting groups and phosphate protecting groups and fluoride treatment to remove the 2'-OH alkylsilyl protecting groups such as the t-butyldimethylsilyl group) are condensed.

Stinchcomb et al., supra describe a time-efficient (approximately 2 hours) one-pot deprotection protocol based on anhydrous methylamine and triethylamine trihydrogen fluoride. Since it has been reported that water contamination during fluoride treatment may be detrimental to the efficiency of the desilylation reaction (Hogrefe et al, 1993, *Nucleic Acids Res.*, 21, 4739–4741), and since the use of aqueous methylamine in combination with TEA.3HF results in ribonucleotide degradation (see Example 3), it has previously been thought necessary to use an anhydrous solution of base such as 33% methylamine in absolute ethanol followed by neat triethylamine trihydrofluoride to effectively deprotect oligoribonucleotides in a one-pot fashion. However, these conditions have proven less than stellar for the complete deprotection of 2'-N-phthaloyl protecting groups, as are used to protect the 2'-amino function of 2'-deoxy-2'-amino nucleoside containing nucleic acid molecules since incomplete deprotection products result (see FIG. 2, compound B). Attempts to force the anhydrous deprotection reaction conditions with longer times and/or higher temperatures for the complete removal of phthaloyl groups results in marked degradation of the ribonucleotide species. Therefore, applicant investigated the use of aqueous methylamine in conjunction with TEA.3HF and DMSO as a one pot method for oligonucleotide deprotection. This method, surprisingly, does not cause the presumed alkaline hydrolysis of ribonucleotide linkages when used in the presence of DMSO. Application of the method without DMSO results in lower yields of full length nucleic acid, presumably from alkaline hydrolysis of ribonucleotide linkages (see Example 3). The one pot aqueous method described herein provides a significantly shorter time for oligonucleotide deprotection and provides material with increased yield and purity when compared to existing two pot aqueous and one pot anhydrous methods.

EXAMPLES

The following are non-limiting examples showing the deprotection of oligonucleotides.

Example 1

Small Scale Deprotection of an Oligonucleotide Comprising One or More Ribonucleotides with 2'-O-TBDMS/N-phthaloyl Protection Using a One-Pot Anhydrous Deprotection Method A ribozyme sequence (Table III) (200 μmole) containing two N-phthaloyl protected 2'-amino nucleosides was synthesized as described herein, on CPG support with a Pharmacia OPII synthesizer. After the synthesis, the support was dried for 15 to 30 min. Approximately 20 mg of the support was transferred to a 5 ml screw capped vial. A 1:1 mixture of 33% methylamine/ethanol (800 μl) and dry DMSO (800 μl) was added to the support and the mixture was heated at 65° C. using a heating block for 15 min. The solution was cooled to rt and then filtered through a 0.5 micron filter into another 5 ml screw capped vial. TEA.3HF (600 μl) was added to the reaction mixture followed by heating at 65° C. for 15 min. The mixture was then cooled and quenched with 50 mM NaOAc (2 ml). The corresponding deprotected, purified full length oligonucleotide was analyzed by Capillary Gel Electrophoresis and ES Mass Spec. The mass spectrum revealed three peaks with masses corresponding to the fully deprotected oligonucleotide, the oligonucleotide with one partially cleaved phthaloyl group intact, and the oligonucleotide with two partially cleaved phthaloyl groups intact (FIG. 3A). The CGE chromatograph indicated a single broad peak (FIG. 4A).

Example 2

Small Scale Deprotection of an Oligonucleotide Comprising One or More Ribonucleotides with 2'-O-TBDMS/N-phthaloyl Protection Using a One-Pot Aqueous Deprotection Method A ribozyme sequence (Table III) (200 μmole) was synthesized as described herein on CPG support with a Pharmacia OPII synthesizer. After the synthesis, the support was dried for 15 to 30 min. Approximately 20 mg of the support was transferred to a 5 ml screw capped vial and the support was heated with aqueous methylamine (1 ml) at 65° C. using a heating block for 15 min. The solution was cooled to rt and then filtered through a 0.5 micron filter into another 5 ml screw capped vial. DMSO (1.6 ml) and TEA.3HF (600 μl) were added to the reaction mixture followed by heating at 65° C. for 15 min. The mixture was then cooled and quenched with 50 mM NaOAc (2 ml). The corresponding deprotected, purified full-length oligonucleotide was analyzed by Capillary Gel Electrophoresis and ES Mass Spec. The mass spectrum revealed one peak with a mass corresponding to the fully deprotected oligonucleotide (FIG. 3B). The CGE chromatograph indicated a single narrow peak (FIG. 4B).

Example 3

Small Scale Deprotection of an Oligonucleotide Comprising One or More Ribonucleotides with 2'-O-TBDMS/N-phthaloyl Protection Using a One-Pot Aqueous Deprotection Method Without DMSO A ribozyme sequence (Table III) (200 μmole) was synthesized as described herein on CPG support with a Pharmacia OPII synthesizer. After the synthesis, the support was dried for 15 to 30 min. Approximately 20 mg of the support was transferred to a 5 ml screw capped vial and the support was heated with aqueous methylamine (1 ml) at 65° C. using a heating block for 15 min. The solution was cooled to rt and then filtered through a 0.5 micron filter into another 5 ml screw capped vial. TEA.3HF (600 μl) was added to the reaction mixture followed by heating at 65° C. for 15 min. The mixture was then cooled and quenched with 50 mM NaOAc (2 ml). The corresponding deprotected, purified full-length oligonucleotide was analyzed by ion exchange HPLC. The HPLC trace revealed significant degradation corresponding to cleavage of ribonucleotide linkages within the oligonucleotide when compared to material from example 2 in which DMSO was used in the deprotection.

Example 4

Large Scale Deprotection of an Oligonucleotide Comprising One or More Ribonucleotides with 2'-O-TBDMS Protection Using a One-Pot Anhydrous Deprotection Method A ribozyme sequence (Table III) (200 μmole) was synthesized as described herein on CPG support with a Pharmacia OPII synthesizer. After the synthesis, the support was dried for 15 to 30 min and transferred to a 500 ml Schott bottle. A 1:1 mixture of 33% methylamine/ethanol (75 ml) and dry DMSO (75 ml) was added to the support and the mixture was heated at 35° C. in an incubated shaker for 4 h. The solution was cooled to rt (15 min) and then filtered through a sintered glass funnel. The support was washed with DMSO (4×15 ml) and the combined filtrate was cooled at −78° C. for 30 min. TEA.3HF (30 ml) was added to the reaction mixture followed by heating at 65° C. for 1 h. The mixture was then cooled at −78° C. for 30 min and quenched with 50 mM NaOAc (200 ml).

Example 5

Large Scale Deprotection of an Oligonucleotide Comprising One or More Ribonucleotides with 2'-O-TBDMS Protection Using a One-Pot Aqueous Deprotection Method A ribozyme sequence (Table III) (200 μmole) was synthesized described herein on CPG support with a Pharmacia OPII synthesizer. After the synthesis, the support was dried for 15 to 30 min and transferred to a 250 ml Schott bottle. 40% Aqueous methylamine (75 ml) was added to the support and the mixture was heated at 35° C. in an incubated shaker for 1 h. The solution was cooled to rt (15 min) and then filtered through a sintered glass funnel. The support was washed with DMSO (4×18.75 ml) and the combined filtrate was cooled at −78° C. for 30 min. TEA.3HF (45 ml) was added to the reaction mixture followed by heating at 65° C. for 1 h. The mixture was then cooled at −78° C. for 30 min and quenched with 50 mM NaOAc (195 ml).

Example 6

Large Scale Deprotection of an Oligonucleotide Comprising One or More Ribonucleotides with 2'-O-TBDMS/N-phthaloyl Protection Using a One-Pot Aqueous Deprotection Method A ribozyme sequence (Table III) (200 μmole) was synthesized as described herein on CPG support with a Pharmacia OPII synthesizer. After the synthesis, the support was dried for 15 to 30 min and transferred to a 250 ml Schott bottle. 40% Aqueous methylamine (75 ml) was added to the support and the mixture was heated at 65° C. in an incubated shaker for 1 h. The solution was cooled to rt (15 min) and then filtered through a sintered glass funnel. The support was washed with DMSO (4×18.75 ml) and the combined filtrate was cooled at −78° C. for 30 min. TEA.3HF (45 ml) was added to the reaction mixture followed by heating at 65° C. for 1 h. The mixture was then cooled at −78° C. for 30 min and quenched with 50 mM NaOAc (195 ml).

Example 7

Large Scale Ion Exchange Purification of an Oligonucleotide Comprising One or More Ribonucleotidess Oligonucleotide comprising one or more ribonucleotidess are purified by ion exchange chromatography following deprotection. The ion-exchange purification process can be performed on both Pharmacia Source Q15 and Biorad Macroprep 25Q type media. The buffer used for equilibration of the purification media is either 20% ethanol (200 proof USP grade) or acetonitrile, in 20 mmolar sodium phosphate and 0.1 M NaCl. The same buffer can be used for loading the nucleic acid molecule onto the purification media, or alternatively, water can be used. The crude oligonucleotide material is loaded on the column in concentrations up to 10 mg/mL. Application of a suitable gradient of an elution buffer such as 1.0 M NaCl can be used to isolate fractions. Following purification, the fractions are analyzed for purity by a suitable method (for example UV, HPLC and/or CGE). The pure fractions are pooled and desalting is performed via tangential flow filtration using membranes such as Sartorius or Pall Filtron PES 1 K membranes. The concentrated material is then lyophilized.

Other Uses

The nucleic acid molecules of this invention (e.g., ribozymes) may be used as therapeutic agents to treat a broad spectrum of diseases and conditions. Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 1987, *Proc. Nat. Acad. of Sci. USA*, 84, 8788, Hazeloff et al., 1988 *Nature*, 234, 585, Cech, 1988, *JAMA*, 260, 3030, and Jefferies et al., 1989, *Nucleic Acid Research*, 17, 1371. Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The nucleic acid molecules of the invention may be used as diagnostic tools to examine genetic drift and mutations within diseased cells or to detect the presence of a particular RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of disease progression by affording the possibility of combinational therapies (e.g., multiple ribozymes targeted to different genes, ribozymes coupled with known small molecule inhibitors, or intermittent treatment with combinations of ribozymes and/ or other chemical or biological molecules). Other in vitro uses of ribozymes of this invention are well known in the art, and include detection of the presence of mRNAs associated with a RNA-related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus, each analysis can require two ribozymes, two substrates and one unknown sample, which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims:

Other embodiments are within the following claims.

TABLE I

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.

TABLE I-continued

Characteristics of naturally occurring ribozymes

Additional protein cofactors required in some cases to help folding and maintainance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [i,ii].
Complete kinetic framework established for one ribozyme [iii,iv,v,vi].
Studies of ribozyme folding and substrate docking underway [vii,viii,ix].
Chemical modification investigation of important residues well established [x,xi].
The small (4–6 nt) binding site may make this ribozyme too non-specific for targeted RNA cleavage, however, the Tetrahymena group I intron has been used to repair a "defective" □-galactosidase message by the ligation of new □-galactosidase sequences onto the defective message [xii].
RNAse P RNA (M1 RNA)

Size: ~290 to 400 nucleotides.
RNA portion of a ubiquitous ribonucleoprotein enzyme.
Cleaves tRNA precursors to form mature tRNA [xiii].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [xiv,xv]
Important phosphate and 2' OH contacts recently identified [xvi,xvii]
Group II Introns Size: >1000 nucleotides.
Trans cleavage of target RNAs recently demonstrated [xviii,xix].
Sequence requirements not fully determined.
Reaction mechanism: 2'-OH of an internal adenosine generates cleavage products with 3'-OH and a "lariat" RNA containing a 3'–5' and a 2'–5' branch point.
Only natural ribozyme with demonstrated participation in DNA cleavage [xx,xxi] in addition to RNA cleavage and ligation.
Major structural features largely established through phylogenetic comparisons [xxii].
Important 2' OH contacts beginning to be identified [xxiii]
Kinetic framework under development [xxiv]
Neurospora VS RNA Size: ~144 nucleotides.
Trans cleavage of hairpin target RNAs recently demonstrated [xxv].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.
Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (viruoids) that use RNA as the infectious agent.
Essential structural features largely defined, including 2 crystal structures [xxvi,xxvii]
Minimal ligation activity demonstrated (for engineering through in vitro selection) [xxviii]
Complete kinetic framework established for two or more ribozymes [xxix].
Chemical modification investigation of important residues well established [xxx].
Hairpin Ribozyme Size: ~50 nucleotides.
Requires the target sequence GUC immediately 3' of the cleavage site.
Binds 4–6 nucleotides at the 5-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite TABLE I-continued Characteristics of naturally occurring ribozymes RNAs of the tobacco ringspot virus, arabis mosaic virus and chicory yellow mottle virus) which uses RNA as the infectious agent.
Essential structural features largely defined [xxxi,xxxii,xxxiii,xxxiv]
Ligation activity (in addition to cleavage activity) makes ribozyme amenable to engineering through in vitro selection [xxxv]
Complete kinetic framework established for one ribozyme [xxxvi].
Chemical modification investigation of important residues begun [xxxvii,xxxviii].

Hepatitis Delta Virus (HDV) Ribozyme

Size: ~60 nucleotides.
Trans cleavage of target RNAs demonstrated [xxxix].
Binding sites and structural requirements not fully determined, although no sequences 5' of cleavage site are required. Folded ribozyme contains a pseudoknot structure [xl].
Reaction mechanism: attack by 2'-OH 5' to the scissile bond to generate cleavage products with 2',3'-cyclic phosphate and 5'-OH ends.
Only 2 known members of this class. Found in human HDV.
Circular form of HDV is active and shows increased nuclease stability [xli]

[i] Michel, Francois; Westhof, Eric. Slippery substrates. Nat. Struct. Biol. (1994), 1(1), 5–7.
[ii] Lisacek, Frederique; Diaz, Yolande; Michel, Francois. Automatic identification of group I intron cores in genomic DNA sequences. J. Mol. Biol. (1994), 235(4), 1206–17.
[iii] Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
[iv] Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
[v] Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
[vi] Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
[vii] Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
[viii] Banerjee, Aloke Raj; Turner, Douglas H.. The time dependence of chemical modification reveals slow steps in the folding of a group I ribozyme. Biochemistry (1995), 34(19), 6504–12.
[ix] Zarrinkar, Patrick P.; Williamson, James R.. The P9.1–P9.2 peripheral extension helps guide folding of the Tetrahymena ribozyme. Nucleic Acids Res. (1996), 24(5), 854–8.
[x] Strobel, Scott A.; Cech, Thomas R.. Minor groove recognition of the conserved G.cntdot.U pair at the Tetrahymena ribozyme reaction site. Science (Washington, D.C.) (1995), 267(5198), 675–9.
[xi] Strobel, Scott A.; Cech, Thomas R.. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
[xii] Sullenger, Bruce A.; Cech, Thomas R.. Ribozyme-mediated repair of defective mRNA by targeted trans-splicing. Nature (London) (1994), 371 (6498), 619–22.
[xiii] Robertson, H. D.; Altman, S.; Smith, J. D. J. Biol. Chem 247, 5243–5251 (1972).
[xiv] Forster, Anthony C.; Altman, Sidney. External guide sequences for an RNA enzyme. Science (Washington, D.C., 1883-) (1990), 249(4970), 783–6.
[xv] Yuan, Y.; Hwang, E. S.; Altman, S. Targeted cleavage of mRNA by human RNase P. Proc. Natl. Acad. Sci. USA (1992) 89, 8006–10.
[xvi] Harris, Michael E.; Pace, Norman R.. Identification of phosphates involved in catalysis by the ribozyme RNase P RNA. RNA (1995), 1(2), 210–18.
[xvii] Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
[xviii] Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.

[xix] Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
[xx] Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
[xxi] Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
[xxii] Michel, Francois; Ferat, Jean Luc. Structure and activities of group II introns. Annu. Rev. Biochem. (1995), 64, 435–61.
[xxiii] Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
[xxiv] Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256 (1), 31–49.
[xxv] Guo, Hans C. T.; Collins, Richard A.. Efficient trans-cleavage of a stem-loop RNA substrate by a ribozyme derived from Neurospora VS RNA. EMBO J. (1995), 14(2), 368–76.
[xxvi] Scott, W. G., Finch, J. T., Aaron, K. The crystal structure of an all RNA hammerhead ribozyme: A proposed mechanism for RNA catalytic cleavage. Cell, (1995), 81, 991–1002.
[xxvii] McKay, Structure and function of the hammerhead ribozyme: an unfinished story. RNA, (1996), 2, 395–403.
[xxviii] Long, D., Uhlenbeck, O., Hertel, K. Ligation with hammerhead ribozymes. U.S. Pat. No. 5,633,133.
[xxix] Hertel, K. J., Herschlag, D., Uhlenbeck, O. A kinetic and thermodynamic framework for the hammerhead ribozyme reaction. Biochemistry, (1994) 33, 3374–3385. Beigelman, L., et al., Chemical modifications of hammerhead ribozymes. J. Biol. Chem., (1995) 270, 25702–25708.
[xxx] Beigelman, L., et al., Chemical modifications of hammerhead ribozymes. J. Biol. Chem., (1995) 270, 25702–25708.
[xxxi] Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
[xxxii] Chowrira, Bharat M.; Berzal-Herranz, Alfredo; Burke, John M.. Novel guanosine requirement for catalysis by the hairpin ribozyme. Nature (London) (1991), 354(6351), 320–2.
[xxxiii] Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
[xxxiv] Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
[xxxv] Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
[xxxvi] Hegg, Lisa A.; Fedor, Martha J.. Kinetics and Thermodynamics of Intermolecular Catalysis by Hairpin Ribozymes. Biochemistry (1995), 34(48), 15813–28.
[xxxvii] Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
[xxxviii] Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
[xxxix] Perrotta, Anne T.; Been, Michael D.. Cleavage of oligoribonucleotides by a ribozyme derived from the hepatitis .delta. virus RNA sequence. Biochemistry (1992), 31(1), 16–21.
[xl] Perrotta, Anne T.; Been, Michael D.. A pseudoknot-like structure required for efficient self-cleavage of hepatitis delta virus RNA. Nature (London) (1991), 350(6317), 434–6.
[xli] Puttaraju, M.; Perrotta, Anne T.; Been, Michael D.. A circular trans-acting hepatitis delta virus ribozyme. Nucleic Acids Res. (1993), 21(18), 4253–8.

TABLE II

A. 2.5 μmol Synthesis Cycle ABI 394 Instrument

| Reagent | Equivalents | Amount | Wait Time* DNA | Wait Time*2-O-methyl | Wait Time* RNA |
|---|---|---|---|---|---|
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

| Reagent | Equivalents | Amount | Wait Time* DNA | Wait Time*2-O-methyl | Wait Time* RNA |
|---|---|---|---|---|---|

B. 0.2 μmol Synthesis Cycle ABI 394 Instrument

| Phosphoramidites | 38.7 | 31 μL | 45 sec | 233 sec | 465 sec |
|---|---|---|---|---|---|
| S-Ethyl Tetrazole | 655 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

C. 0.2 μmol Synthesis Cycle 96 well Instrument

| Reagent | Equivalents DNA/2'-O-methyl/Ribo | Amount DNA/2'-O-methyl/Ribo | Wait Time* DNA | Wait Time*2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 μL | 100 sec | 200 sec | 200 sec |
| Acetonitrile | NA | 1150/1150/1150 μL | NA | NA | NA |

*Wait time does not include contact time during delivery.

TABLE III

Nucleic Acid Sequence used in Deprotection Studies

| Sequence | RPI No. | Seq ID No. |
|---|---|---|
| g$_s$c$_s$a$_s$g$_s$ug GccgaaagGCGaGuGaGGuCu agcuca B | 19292 | 1 |

What we claim is:

1. A process for synthesis, one-pot deprotection, and purification of a nucleic acid molecule having one or more ribonucleotides, comprising the steps of:
   a) synthesizing said nucleic acid molecule using a method selected from the group consisting of solid phase phosphoramidite, solution phase phosphoramidite, solid phase H-phosphonate, solution phase H-phosphonate, hybrid phase phosphoramidite, and hybrid phase H-phosphonate-based synthetic methods;
   b) contacting said nucleic acid molecule from step (a) with aqueous alkylamine, trialkylamine, or a mixture of alkylamine and trialkylamine, under conditions suitable for the removal of any 2'-amino protecting groups, exocyclic amino (base) protecting groups and/or phosphate protecting groups, which may be individually present or absent, from said molecule;
   c) contacting reaction mixture having said nucleic acid molecule from step (b) with a mixture of polar solvent and trialkylamine•hydrogen fluoride under conditions suitable for the removal of a 2'-OH protecting group;
   d) loading reaction mixture having said nucleic acid molecule from step c) onto ion-exchange purification media in a suitable buffer comprising buffers selected from the group consisting of water, 20% ethanol in about 20 mM sodium phosphate and about 0.1 M NaCl and acetonitrile in about 20 mM sodium phosphate and about 0.1 M NaCl;
   e) applying a purification gradient using a suitable elution buffer, analyzing the fractions and allowing for the Pure fractions to be pooled and desalted.

2. The process of claim 1, wherein said nucleic acid molecule comprising one or more ribonucleotides is an enzymatic nucleic acid molecule.

3. The process of claim 1, wherein said aqueous alkylamine is aqueous methylamine.

4. The process of claim 1, wherein said aqueous alkylamine is 40% aqueous methylamine.

5. The process of claim 1, wherein said aqueous alkylamine is aqueous ethylamine.

6. The process of claim 1, wherein said aqueous trialkylamine is triethylamine.

7. The process of claim 1, wherein said trialkylamine.trihydrofluoride is triethylamine.trihydrofluoride (TEA.3HF).

8. The process of claim 1, wherein said suitable conditions to remove said 2'-amino protecting groups, exocyclic amino (base) protecting groups and/or phosphate protecting groups, which may be individually present or absent, from said molecule comprise contacting said nucleic acid molecule comprising one or more ribonucleotides with aqueous methylamine at a temperature of between 20° C. and 80° C. and for a time of between 15 and 120 minutes.

9. The process of claim 1, wherein said suitable conditions to remove said 2'-OH protecting group comprise contacting said nucleic acid molecule with said polar solvent and triethylamine.hydrogen fluoride (TEA.3HF) at a temperature between 30° C. and 100° C. and for a time of between 30 and 120 minutes.

10. The process of claim 8, wherein said temperature is about 35° C. and said time is about 60 minutes.

11. The process of claim 8, wherein said temperature is about 35° C. and said time is about 60 minutes.

12. The process of claim 9, wherein said temperature is about 65° C. and said time is about 60 minutes.

13. The process of claim 1, wherein said polar solvent is selected from the group consisting of DMSO, DMF, ethyl alcohol, methyl alcohol, isopropyl alcohol, and N-methylpyrrolidinone.

14. The process of claim 1, wherein said polar solvent is used in a 1:1 ratio with said aqueous methylamine.

15. The process of claim 1, wherein said alkylamine and said trialkylamine reaction mixture is filtered prior to treatment with said polar solvent and trialkylamine.hydrogen fluoride.

16. The process of claim 1, wherein said nucleic acid molecule from step (b) is filtered and washed with said polar solvent from step (c), prior to step (c).

17. The process of claim 1, wherein said nucleic acid molecule is synthesized on controlled pore glass (CPG) support.

18. The process of claim 1, wherein said nucleic acid molecule is synthesized on polystyrene (PS) support.

19. The process of claim 1, wherein said trialkylamine.hydrogen fluoride reaction is quenched with sodium acetate.

20. The process of claim 19, wherein said sodium acetate is aqueous sodium acetate.

21. The process of claim 19, wherein said trialkylamine.hydrogen fluoride reaction is cooled to about −78° C. prior to said quench with sodium acetate.

22. The process of claim 1, wherein said 2'-amino protecting group comprises the N-phthaloyl protecting group.

23. The process of claim 1, wherein said 2'-amino protecting group comprises the FMOC protecting group.

24. The process of claim 1, wherein said 2'-OH protecting group comprises the t-butyldimethylsilyl (TBDMSi) protecting group.

* * * * *